US008277430B2

(12) United States Patent
Tabor et al.

(10) Patent No.: US 8,277,430 B2
(45) Date of Patent: Oct. 2, 2012

(54) ABSORBENT GARMENT WITH STRAND COATED ADHESIVE COMPONENTS

(75) Inventors: Jeffery M. Tabor, Appleton, WI (US); Melanie Milslagle, Appleton, WI (US); Joseph A. Mlinar, Appleton, WI (US); Thomas J Vanselow, Appleton, WI (US)

(73) Assignee: Kimberly-Clarl Worldwide, Inc., Neenah, WI (US)

( * ) Notice: Subject to any disclaimer, the term of this patent is extended or adjusted under 35 U.S.C. 154(b) by 1806 days.

(21) Appl. No.: 11/024,954

(22) Filed: Dec. 28, 2004

(65) Prior Publication Data

US 2006/0142728 A1 Jun. 29, 2006

(51) Int. Cl.
*A61F 13/15* (2006.01)
(52) U.S. Cl. ......... 604/385.24; 604/385.25; 604/385.26; 604/385.27; 604/385.29
(58) Field of Classification Search ............. 604/385.24, 604/385.25, 385.26, 385.27, 385.29
See application file for complete search history.

(56) References Cited

U.S. PATENT DOCUMENTS

| 4,634,482 | A | * | 1/1987 | Lammers ...................... 156/164 |
| 4,666,542 | A | | 5/1987 | De Jonckheere |
| 4,687,477 | A | | 8/1987 | Suzuki et al. |
| 4,762,582 | A | | 8/1988 | De Jonckheere |
| 4,842,666 | A | | 6/1989 | Werenicz |
| 4,842,666 | A | | 10/1992 | Werenicz |
| 5,163,932 | A | | 11/1992 | Nomura et al. |
| 5,340,648 | A | | 8/1994 | Rollins et al. |
| 5,415,649 | A | | 5/1995 | Watanabe et al. |
| 5,449,353 | A | | 9/1995 | Watanabe et al. |
| 5,501,756 | A | | 3/1996 | Rollins et al. |
| 5,507,909 | A | | 4/1996 | Rollins et al. |
| 5,622,581 | A | | 4/1997 | Ducker et al. |
| 5,749,865 | A | * | 5/1998 | Yamamoto et al. ....... 604/385.29 |
| 5,817,087 | A | | 10/1998 | Takabayashi et al. |
| 5,876,392 | A | | 3/1999 | Hisada |
| 5,904,675 | A | | 5/1999 | Laux et al. |
| 6,049,916 | A | * | 4/2000 | Rajala et al. ...................... 2/400 |

(Continued)

FOREIGN PATENT DOCUMENTS

EP 0 950 436 A2 10/1999

(Continued)

OTHER PUBLICATIONS

Photos of Assurance® Disposable Protective Underwear Packaging, manufactured by Tyco/Healthcare/Kendall Co., 601 Allendale Road, King of Prussia, PA 19406 (2 pages) (prior to Dec. 2004).

(Continued)

*Primary Examiner* — Jacqueline F. Stephens
(74) *Attorney, Agent, or Firm* — R. Joseph Foster, III (57) ABSTRACT

An absorbent garment includes a body panel having a terminal waist edge, at least first and second layers terminating at the terminal waist edge and at least one elastic element disposed between the first and second layers. The body panel has at least first and second adhesive regions. The first adhesive region is defined by the at least one elastic element, which is strand coated with a first adhesive. The second region is defined by a control coating of a second adhesive applied between the first and second layers. In one embodiment, the first region has a greater sensory softness than the second region. In one embodiment, the body panel, in an unstretched condition, has a surface softness with a mean deviation of coefficient of friction less than about 0.020 in the first adhesive region.

14 Claims, 5 Drawing Sheets

U.S. PATENT DOCUMENTS

| | | | |
|---|---|---|---|
| 6,077,375 | A | 6/2000 | Kwok |
| 6,197,406 | B1 | 3/2001 | Kwok |
| 6,200,635 | B1 | 3/2001 | Kwok |
| 6,235,137 | B1 | 5/2001 | Van Eperen et al. |
| 6,361,634 | B1 | 3/2002 | White et al. |
| 6,375,646 | B1 | 4/2002 | Widlund et al. |
| 6,394,991 | B1 | 5/2002 | Takei et al. |
| 6,461,430 | B1 | 10/2002 | Kwok |
| 6,482,195 | B1 | 11/2002 | Kumasaka |
| 6,491,776 | B2 | 12/2002 | Alper et al. |
| 6,509,089 | B1 | 1/2003 | Rollins et al. |
| 6,520,237 | B1 | 2/2003 | Bolyard, Jr. et al. |
| 6,582,518 | B2 | 6/2003 | Riney |
| 6,610,161 | B2 | 8/2003 | Erdman |
| 6,613,146 | B2 | 9/2003 | Bolyard, Jr. |
| 6,652,693 | B2 | 11/2003 | Burriss et al. |
| 6,719,846 | B2 | 4/2004 | Nakamura et al. |
| 6,737,102 | B1 | 5/2004 | Saidman et al. |
| 2001/0030014 | A1 | 10/2001 | Kwok |
| 2001/0054477 | A1 | 12/2001 | Kwok |
| 2002/0049421 | A1 | 4/2002 | Hayase et al. |
| 2002/0052588 | A1 | 5/2002 | Otsubu |
| 2002/0148550 | A1 | 10/2002 | Suzuki |
| 2004/0003670 | A1 | 1/2004 | Minerath, III et al. |

FOREIGN PATENT DOCUMENTS

| | | |
|---|---|---|
| EP | 0 866 682 B1 | 3/2000 |
| EP | 0 950 436 A3 | 11/2000 |
| JP | 06-311999 A | 11/1994 |
| JP | 2003-265520 A | 9/2003 |
| WO | WO 87/04117 | 7/1987 |
| WO | WO 03/003963 A | 1/2003 |
| WO | WO 039422 A | 5/2003 |
| WO | WO 03/051256 A1 | 6/2003 |
| WO | WO 2006/071345 A1 | 7/2006 |

OTHER PUBLICATIONS

Photo of body side view of Assurance® Disposable Protective Underwear, manufactured by Tyco/Healthcare/Kendall Co., 601 Allendale Road, King of Prussia, PA 19406 (1 page) (prior to Dec. 2004).

Photos of Assurance® Disposable Protective Underwear waist band region under a black light (3 pages) (Aug. 2005).

International Search Report in International Application No. PCT/US2005/038412, mailed May 30, 2006, 6 pages.

Written Opinion in International Application No. PCT/US2005/038412, dated May 30, 2006, 9 pages.

* cited by examiner

ABSORBENT GARMENT WITH STRAND COATED ADHESIVE COMPONENTS

The present invention relates generally to an absorbent garment, and in particular, to an absorbent garment having strand coated elastic elements.

BACKGROUND

Absorbent garments can be configured in many different forms. For example, absorbent garments can be configured as a pant-type, pull-on garment, or as a diaper-type product that is drawn up between the legs and fastened about the waist with various fastening systems. Typically, such absorbent garments are configured with a chassis that fits around the body of the user. In some garments, the chassis includes one or more body panels that are formed from at least two layers of material, with one or more elastic elements disposed between the layers. Typically, one or more of the chassis layers is covered with a coating of adhesive that secures the layers and elastic element(s) in a laminate structure. In other garments, the elastic elements are strand coated with an adhesive and disposed between the layers of material. In some instances, the adhesive coverage can lead to a chassis that is relatively stiff and lacking in softness in certain areas, or that lacks requisite strength properties or manufacturing efficiencies in other areas of the garment.

SUMMARY

Briefly stated, in one aspect, an absorbent garment includes a body panel having a terminal waist edge, first and second layers each terminating at the terminal waist edge, and at least one waist elastic element disposed between the first and second layers and extending in a lateral direction parallel to the terminal waist edge. The body panel has at least first and second adhesive regions. The first adhesive region is defined by the at least one elastic element, which is strand coated with a first adhesive. The second adhesive region is defined by a control coating of a second adhesive applied between the first and second layers. In one embodiment, the first adhesive region extends to the terminal waist edge, and does not have any adhesive other than the strand coated adhesive.

In another aspect, a method of assembling an absorbent garment include strand coating at least one elastic element with a first adhesive and applying a control coating of a second adhesive to a portion of one or both of first and second layers of web material. The method further includes disposing at least one elastic element between the first and second layers of web material and joining the first and second layers of web material with the at least one elastic element strand coated with the first adhesive and the control coating of the second adhesive.

In yet another aspect, an absorbent garment includes a body panel stretchable between an unstretched condition and a stretched condition. The body panel includes first and second layers of spunbond material and a plurality of elastic elements disposed between the first and second layers in a spaced apart relationship. Each of the plurality of elastic elements has a strand coating of adhesive. The plurality of elastic elements define an adhesive region, wherein the body panel, in the unstretched condition, has a surface with a mean deviation of coefficient of friction less than about 0.020 in the adhesive region.

The absorbent garments and methods disclosed herein provide significant advantages over other absorbent garments and methods for the use and manufacture thereof. For example, the joining of body panel layers with a combination of strand coated elastic elements and control coating provides improved softness in a predetermined area of the garment while maintaining a requisite strength and integrity and/or ease of manufacturing in other predetermined areas. Moreover, by varying the spacing of the elastic elements and the amount of strand coating, the softness of the body panel can be greatly improved without sacrificing the overall robustness of the garment.

The foregoing paragraphs have been provided by way of general introduction and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

DETAILED DESCRIPTION OF THE PRESENTLY PREFERRED EMBODIMENTS

Figure 2:
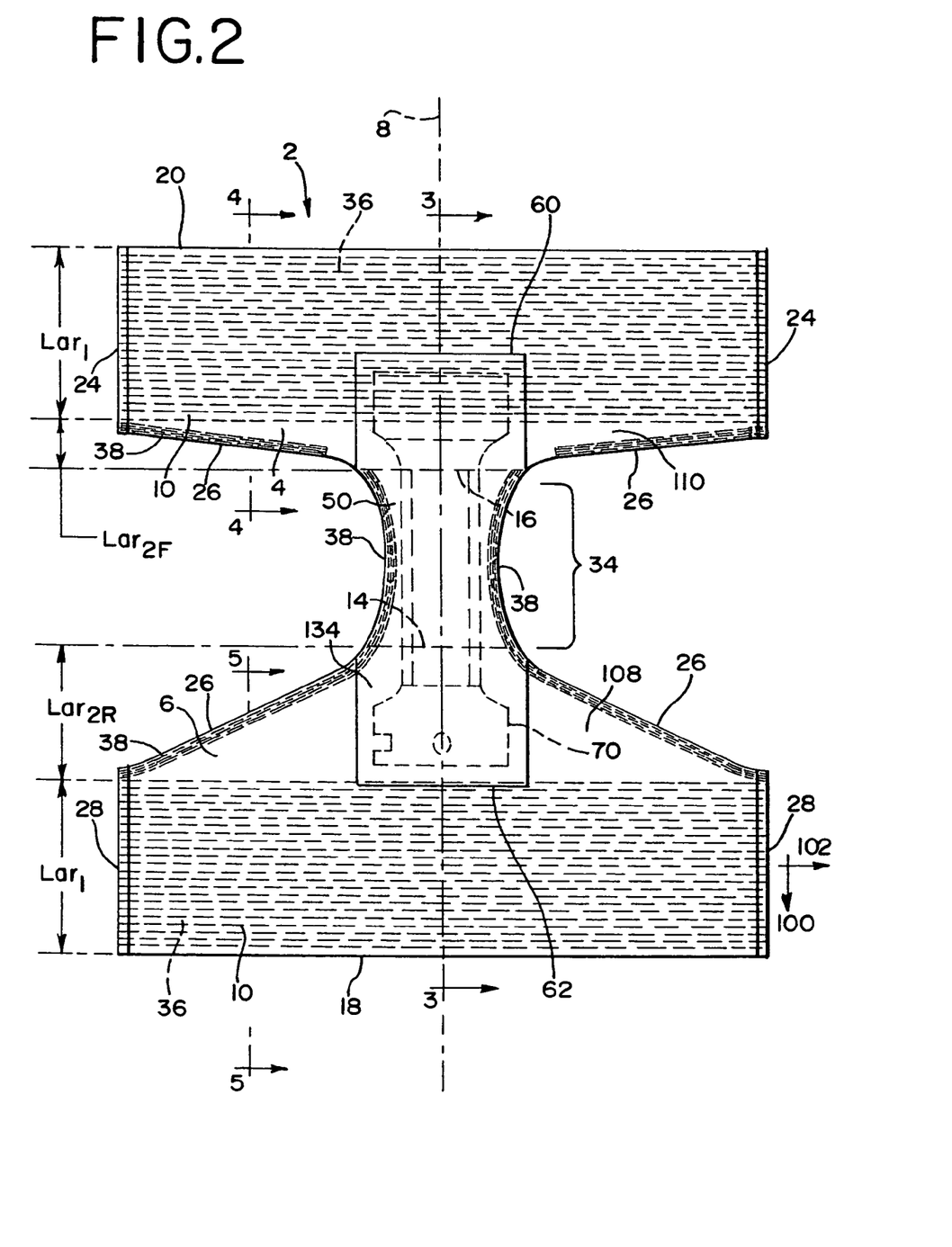
FIG. 2 is a plan view of an absorbent garment in a flat, unfolded condition prior to the side seams being joined.

With reference to FIG. 2, it should be understood that the term "longitudinal," as used herein, means of or relating to length or the lengthwise direction 100, and in particular, the direction running between the front and back of the user. The term "laterally," as used herein means situated on, directed toward or running from side to side, and in particular, a direction 102 running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside" which means the side closest to the body of the user, while the terms "outer" and "lower" refer to a "garment side."

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

Referring to FIGS. 2-5, an absorbent garment 2 includes a first, front body panel 4 and a second, rear body panel 6. The first and second body panels each have an inner, bodyside surface 10 and an outer, garment side surface 12. The first, front body panel 4 has a terminal edge 20 defining a waist edge of the front body panel. At least one layer of the front body panel 4 also has a terminal edge 16 defining a crotch edge of the front body panel. Likewise, the second, rear body panel 6 has a terminal edge 18 defining a waist edge of the rear body panel, with at least one layer of the body panel further having a terminal edge 14 defining a crotch edge of the body panel. Each of the first and second body panels has an outboard edge 24, 28 formed along the outer periphery of laterally opposed side portions of the first and second body panel.

As shown in FIG. 2, the first and second body panels 4, 6 have tapered edges 26 defining the leg opening. It should be understood that in an alternative embodiment the edges can run parallel to each other in the lateral direction 102, or one of the edges can be tapered with the other running parallel to the lateral direction. The terminal edges 14, 16 of at least one layer of each of the first and second body panels are longitudinally spaced to form an opening 34 therebetween in the crotch region of the garment, while the second terminal edges 20, 18 of the first and second body panels form front and back waist edges respectively. One or more leg elastic elements 38 can be secured along the inner terminal edges of the body panels 4, 6 and along the side edges of a crotch portion of the garment, and in particular an absorbent composite 50, to form a gasket with the leg of the user.

Referring to FIGS. 1-5, one or more, and desirably a plurality, meaning two or more, laterally extending elastic elements 36 are secured to each of the first and second body panels along the terminal edges 20, 18. In one exemplary embodiment, a plurality of laterally extending elastic elements is longitudinally spaced across a portion of the waist region of each of the front and rear body panels 4, 6. In one embodiment, the leg elastics 38 secured along the terminal edges of the body panels are spaced from and do not intersect the waist elastic elements 36, with the leg elastics 38 and the waist elastic elements 36 being retained by different adhesive technologies as explained below.

In one exemplary embodiment, each body panel 4, 6 includes 23 elastic elements, or strands, longitudinally spaced over a length of about 7.22 inches. The various waist and leg elastic elements can be formed from rubber or other elastomeric materials. One suitable material is a Lycra® elastic material. In one embodiment, the elastic elements are made of a Creora Spandex 940 decitex, which corresponds to a diameter of about 0.016 inches per strand. In another embodiment, each body panel has 27 elastic strands spaced over a length of 8.53 inches. The elastic elements 36 allow for the body panels to be stretched in a lateral direction 102 between an unstretched and stretched condition, wherein the body panel is stretched to 120% of its unstretched length.

Figure 1:
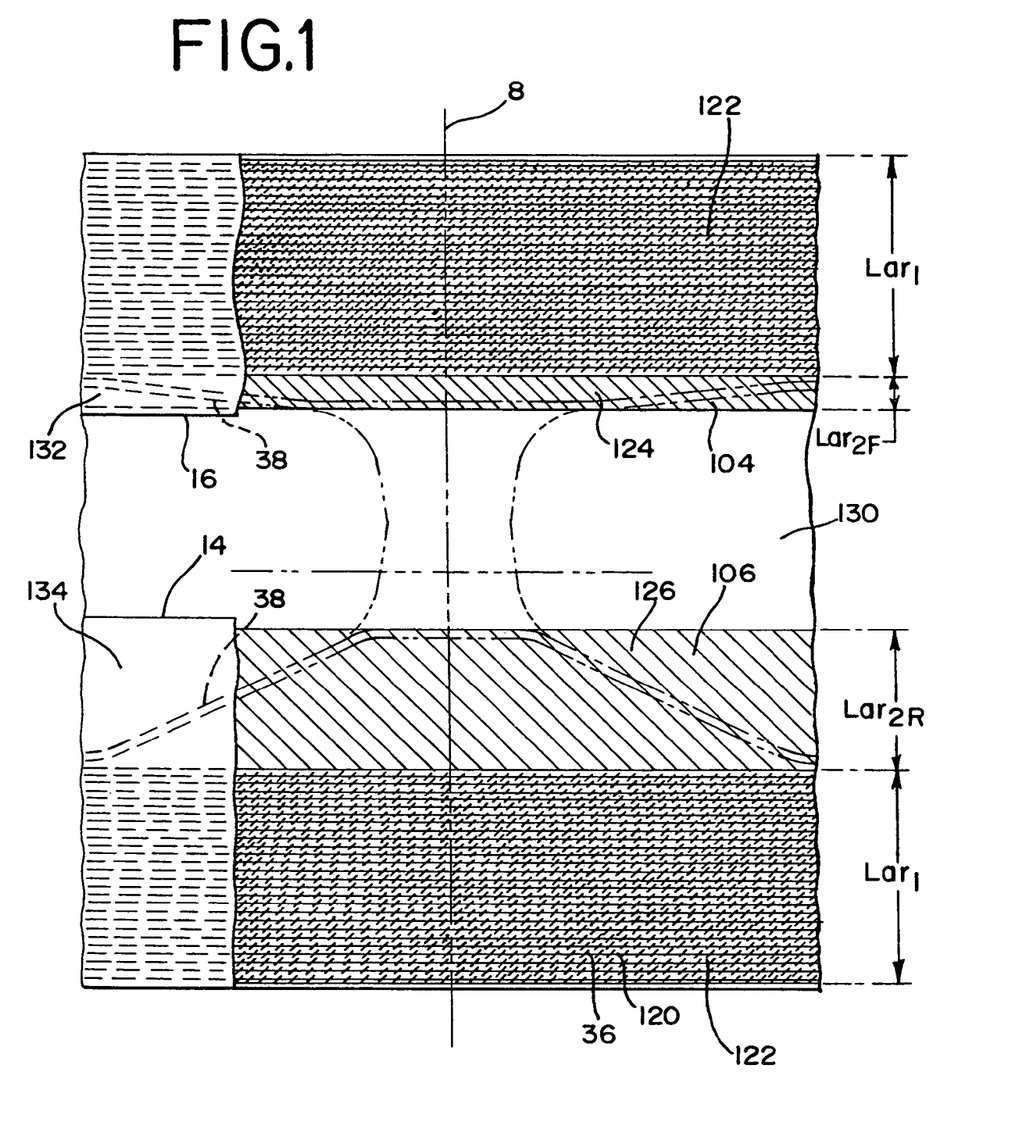
FIG. 1 is a plan view of a first body panel layer with first and second adhesive regions with second body panel layers shown in partial cut-away.

Referring to FIGS. 1 and 2, in one embodiment, a non-elasticized area 108, 110 is formed between the elastic elements 36 extending along the upper waist portion of each of the front and rear body panels 4, 6 and the elastic elements 38 extending along the lower terminal edges 14, 16 defining the leg opening. In one embodiment, a portion of the waist elastic strands 36 are deadened, for example in the area overlying the retention portion on the first body panel 4, so as to form a non-elasticized area 107.

As shown in the embodiment of FIGS. 2-5, each body panel 4, 6 is formed as a composite or laminate material formed from at least two non-woven layers 112, 114, 116, otherwise referred to as substrates or laminates, with the plurality of elastic strands 38, 36 sandwiched therebetween. The two or more layers are bonded with various adhesives, such as hot melt, or by other techniques, including for example and without limitation ultrasonic bonding and heat pressure sealing. As shown in FIGS. 1-5, the inner layers 112, 116 or liners, defines the terminal crotch edges 16, 14 and waist edges 20, 18 of the rear and front body panels 6, 4. The outer layer 114, or outer cover, extends the entire length of the garment and further defines a crotch region 118 thereof. In one embodiment, all of the layers 112, 114, 116 have a free edge or terminate at the terminal waist edges 20, 18. The layers 112, 114 also have a free edge, or terminate at the terminal crotch edges 16, 14. It should be understood that the outer layer could be formed as two separate, longitudinally spaced pieces that mate with the corresponding liner layers and terminate at the crotch edges of the inner liner layers, with the absorbent composite bridging and connecting the front and rear body panels.

Referring to FIGS. 1-6, each of the elastic elements 36 are individually strand coated with a strand coating of adhesive 120. In one embodiment, a Nordson Surewrap™ adhesive technology is used to strand coat the elastic elements. Various coating methods and techniques, including strand coating methods and techniques, are shown for example in U.S. Pat. Nos. 5,340,648, 5,501,756, 5,507,909, 6,077,375, 6,200,635, 6,235,137, 6,361,634, 6,561,430, 6,520,237, 6,582,518, 6,610,161, 6,613,146, 6,652,693, 6,719,846 and 6,737,102, all of which are hereby incorporated herein by reference.

Figure 6:
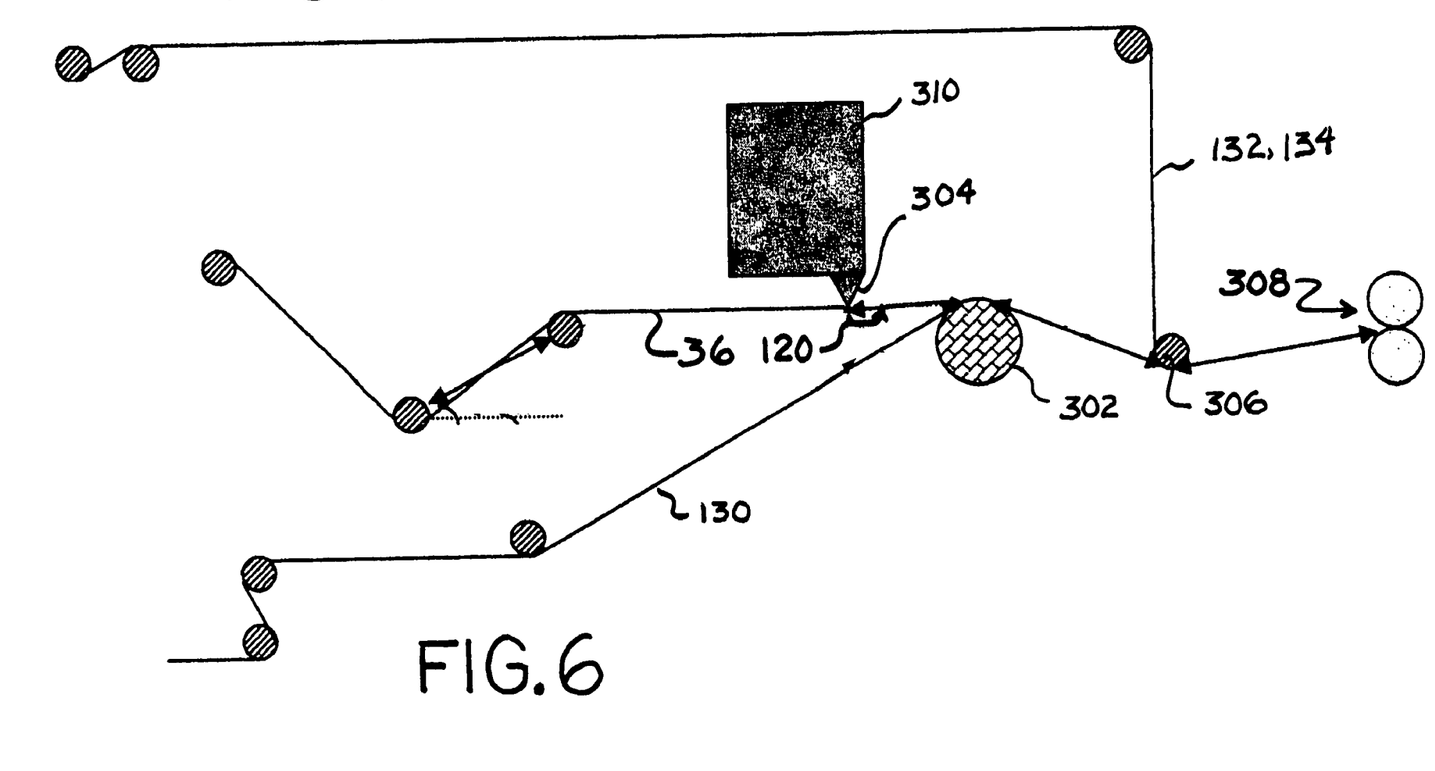
FIG. 6 is a side view of a system for applying a strand-coating to an elastic element.

Referring to FIG. 6, the elastic elements 36, with the strand coating 120 applied thereto, are disposed between the layers of the body panel, such that the strand coated elastic elements 36 join the layers together. In particular, a first web 130 is introduced to a combining roll 302. The strand coating 120 is applied to the elastic elements, 36 with an applicator 310 including one or more nozzles 304 in front of the combining roll. The coated strand is then applied to the web 130 at the combining roll, with the web and applied strand then introduced to a second combining roll 306. The second web 132, 134 is also introduced to the second combining roll 306 and joined to the first web with the strand coated elastic elements disposed therebetween. The laminate is then introduced to a nip 308. The elastic strand, with the strand coating 120 is bonded to both the first and second webs 132, 134.

As shown in FIG. 1, the portion of the body panel secured with the strand coated elastic elements is defined as a first adhesive region 122 having a length $L_{ar1}$. It should be understood that the length $L_{ar1}$ can be different for the front and rear body panels. In one embodiment the first adhesive region extends to the terminal waist edges 18, 20 of each body panel. Each adhesive region has a corresponding adhesive coverage which is the area covered by the strand coated adhesive. In particular, the amount of adhesive coverage (AC) as a percentage of the area of the adhesive region, is calculated by the following formula:

$$AC(\%) = \{d*N/[d*N+s*(N-1)]\}*C*100$$

C=assumed adhesive coverage of each strand
d=diameter of strand
s=spacing between strands
N=number of strands In one embodiment, described above, wherein 23 elastic strands, each with a diameter of 0.016 inches, are spaced over a length of 7.22 inches, the adhesive coverage (AC), depending on C, is from about 0.25% to about 5.1% (maximum where C=1) of the area of the adhesive region. In another embodiment, described above, wherein 27 elastic strands, each with a diameter of 0.016 inches are spaced over a length of 8.53 inches, the coverage, depending on C, is from about 0.20% to about 4.1% (maximum where C=1) of the area of the adhesive region. In various embodiments, the adhesive coverage is from about 0.10% to about 6.00% of the area of the adhesive region. In one embodiment, the strand coated elastic elements 36 are the only adhesive component joining the layers 112, 116, 114 of the body panel in the first adhesive region 122, which extends to the terminal waist edge of the body panels 4, 6 as explained above.

In this way, the application of adhesive in the spaces between the elastic elements is eliminated, which provides a softer, more cloth-like feel. In various embodiments, the spacing between the strand coated elastic elements is between about 5 mm and about 15 mm, and suitably between about 6.50 mm and about 12.50 mm, and includes spacings of 5.00 mm, 5.56 mm, 6.25 mm, 6.50 mm, 6.67 mm, 7.41 mm, 7.50 mm, 8.33 mm, 10 mm, 11.11 mm, 12.50 mm and 15.00 mm. Of course, other spacings may also be suitable.

In other embodiments, a control coating of adhesive is also applied in the first adhesive region. The coating can be in the form of a continuous coat of adhesive, a swirl pattern, or other types of coating.

Referring to the embodiment of FIGS. 1 and 2, the portions of the body panel between the first adhesive region 122 and the crotch edges 14, 16 of the body panel layer 112, 116 is formed by joining the layers 112, 116, 114 with a control coating 124, 126 of adhesive in second adhesive regions 104, 106, having respective lengths $L_{ar2F}$ and $L_{ar2R}$. This control coating 124, 126 is further used to adhere the leg elastic elements 38 between the two layers 112, 116, 114 of the body panels 4, 6. In this way, the waist region, or first adhesive region 122 of the front and rear body panels is provided with a greater softness, while the control coat in the second adhesive regions 104, 106 facilitates the manufacturing process by allowing the leg elastics 38 to be placed into the product without excess adhesive buildup. In one embodiment, the same adhesive is used for the strand coating in the first adhesive region and the control coating in the second adhesive region. In another embodiment, different adhesives are used for the strand coating and control coating.

After the elastic elements 36 are strand coated and one or both of the body panel layers are control coated in the second adhesive regions 104, 106, the layers 112, 114, 116 are joined together with the elastic elements 36, 38 disposed therebetween. The body panel layers 112, 114, 116 are run through a combining nip, which laminates the body panel web composite and bonds the strand coated elastic elements to both layers of the body, panel. As shown in FIG. 1, a web 130 defining the outer cover layer 114, as well as portions of the liner webs 132, 134 are cut, for example by die cutting, to form the leg openings and crotch portion of the garment.

The body panel layers, including the inner liner 114, 116 and the outer cover 112, are preferably made of a relatively homogenous non-woven material, whether made of one or more layers or substrates, and preferably without any additional film materials or other types of materials being laminated thereto. As such, the body panels can be made with a relatively low basis weight, yet still exhibit requisite strength properties while remaining relatively soft to the touch. It should be understood that the body panels can be formed from more than two layers or substrates. Of course, it should be understood that the body panels can be made up at least in part from other materials, including various knitted or woven fabrics, polymer films, laminates and the like. In one embodiment, the non-woven layers or substrates are made of a spunbond material, for example a 0.55 osy wire-weave spunbond material.

The softness of the body panels can be determined in a variety of different ways, including sensory testing. One test method is the Kawabata surface friction test, which demonstrates differences in the laminate surface softness by measuring the mean deviation of the coefficient of friction. In particular, the lower the mean deviation, the smoother/softer the surface, as correlated with additional sensory testing.

The Kawabata surface friction best uses a Kawabata Evaluation System (KES-SE) surface friction electronic instrument manufactured by Kato Tech Company, Japan, and which is equipped with a calculation circuit to measure frictional coefficient (MIU) and the mean deviation of the coefficient of friction (MMD) of sheet-like materials.

During the test, a specimen is placed on a sliding table at a specified speed. The moving direction and distance are detected by a potentiometer as the displacement output voltage. Surface friction is measured by a roughness sensor positioned against the specimen surface, or by using a frictional force sensor with weight. The frictional force sensor is connected to a frictional force transducer with a linear differential transformer. The measured values are closely related to the hand touch feeling of a material's surface. In particular, a KES Surface Friction and Surface Roughness Electronic Unit (KES-SE-U) is used, together with a KES Surface Friction and Surface Roughness Mechanical Unit (KES-SE-U) which includes a 50-gram sensor weight, and a specimen fixation weight. The testing laboratory has a conditioned testing environment of $23\pm2°$ C. and $50\pm2°$ C. and $50\pm5\%$ relative humidity. The probe for measuring friction consists of 10 stainless steel wires each with a diameter of 0.5 mm and a length of 10 mm. The required number of specimens is cut from a sample. Each specimen is cut to a dimension of approximately 10 by 10 centimeters, or in one embodiment 10 cm in the machine direction by 6 cm in the cross direction, with the surface testing being performed only in the machine direction and with the sample mounted such that the machine direction is parallel to the moving direction of the bed. The measured distance on the sample is 2 cm.

The test is run according to the following steps:

1. The cable labeled FR on the mechanical unit is connected to the FR-DT port located in back of the KES unit.
2. The analog meter for surface friction is positioned on the left side of the electronic unit and is labeled FRICTION. The zero adjust dial for surface friction testing is labeled FR-ZERO.
3. Press the black button labeled FR-T.
4. Turn the CHECK OSC/BAL/MES knob to OSC. The needle of each analog meter should be positioned at approximately 10 volts. If the deviation is larger than 2 volts, do not use the equipment; repair is required.
5. Position the FRIC DT/GU knob to DT.
6. Toggle the SENS switch to the appropriate position; e.g., the H position or the L Position.
7. Turn the CHECK OSC/BAL/MES knob to BAL. The needle on the analog meter labeled FRICTION should be positioned at $0\pm1$ volt. When it is necessary to adjust the BAL, use a small screwdriver and adjust the FR-BAL and FRC-BAL in the following order: first adjust the FR-BAL, and then adjust the FRC-BAL.

8. Turn the CHECK OSC/BAL/MES knob to MES. The digital readout should display ±00.00 volt. If it is necessary to adjust the MES, unlock the zero adjust dial labeled FR-ZERO, make the necessary adjustment, and relock the dial.

9. Turn the SPEED knob to one of the following selections: 1, 2, 5, or 10 mm/s to set the testing speed. The standard setting for the SPEED knob is 1 mm/s. Toggle the SPEED switch to either 1/10 or 1 to adjust the speed knob selection. The standard setting for the SPEED switch is 1.

10. Remove the screws to the specimen fixing chuck and remove the specimen fixing chuck from the specimen table.

11. While holding the white knob of the frictional force detector housing, loosen the fixing screw and adjust the sensor hanging shaft height so the center of the frictional force sensor hanging shaft is approximately aligned horizontally with the top of the specimen table. Once approximately aligned, tighten the fixing screw.

12. Place the specimen fixing chuck on the specimen table. Place the screws in the specimen fixing chuck, and tighten sufficiently so the specimen fixing chuck remains in place.

13. Select the KES program by double-clicking the KES TEST Ver 6.36 icon.

14. Select Tester(S) from the menu bar at the top of the KES-FB System Measurement Program screen.

15. Select SE and Friction Measure from the drop-down menu.

16. Friction Sensitivity: When H is selected on the electronic unit, select H as a standard setting. When L is selected on the electronic unit, select L as a standard setting.

17. Speed: Select the appropriate speed; 1 and 1 are standard settings.

18. Friction Static Load: Select 50 as a standard input value if using the sensor weight. Select 25 as the standard input value if the sensor is used without the sensor weight.

19. Loosen the screws on the specimen fixing chuck sufficiently that the specimen can be positioned under the chuck. Lift the top of the fixing chuck; place the specimen on the specimen table and under the chuck so that it is approximately centered on the specimen table. Tighten the specimen fixing chuck screws sufficiently to hold the specimen firmly in place. Avoid touching the test areas.

20. Place the specimen fixation weight over the specimen, so the narrow side of the specimen fixation weight is approximately centered between the specimen fixing chuck screws and aligned approximately 1 cm from the right edge of the specimen fixing chuck.

21. Ensure the digital display reads ±00.00 volt. If it does not, unlock the zero adjust dial labeled FR-ZERO, make the necessary adjustment, and relock the dial.

22. Carefully place the frictional force sensor onto the sensor hanging shaft.

23. Ensure the frictional force sensor is properly seated on the hanging shaft by placing a finger lightly on the frictional force sensor's free end. When the frictional force sensor is properly seated, ensure the digital readout displays ±00.00 volt. If necessary, carefully reposition the frictional force sensor.

24. Select WARP for the MD testing or WEFT for the CD testing on the computer.

25. Select Measure(M) from the menu bar at the top of the screen.

26. Select Manual Start from the drop-down menu.

27. Press the black button labeled SR-T.

28. Press the black button labeled FR-T.

29. Press the black button labeled MIU.

30. Click OK or press either the Enter key or spacebar.

31. Electronic unit: Press and hold for approximately 1 second the green button labeled MES START. The specimen table on the mechanical unit will begin to move. A graph will display as the test runs. At the completion of the test, the results will display.

32. Record the coefficient of friction (MIU1) in the forward direction (INT) to the nearest 0.01 unit.

33. Record the mean deviation of the coefficient of friction (MMD1) in the forward direction (INT) to the nearest 0.01 unit.

34. Record the static load in grams.

35. Record the speed in mm/second.

36. Record the sensitivity as H or L.

37. Report the coefficient of friction value (MIU1) to the nearest 0.001 unit by multiplying by the appropriate factor. For the load set at 50 g, speed at 1 mm/s and sensitivity=H, the factor for MIU is 0.1 and the factor for MMD is 0.01.

38. Report the mean deviation of MIU (MMD1) to the nearest 0.0001 unit by multiplying by the appropriate factor.

As shown in Table 1, the mean deviation for each sample of material was lowered when the layers were joined by strand coating as opposed to control coating. The mean deviation was calculated for each sample in a stretched (120% of unstretched length) and unstretched condition.

TABLE 1

COEFFICIENT OF FRICTION AND MEAN DEVIATIN OF MIU
Static Load = 50 g
Speed = 1 mm/s
Sensitivity = H

| | Unstretched | | Stretched | |
| --- | --- | --- | --- | --- |
| Product | Coefficient of Friction | Mean Deviation of MIU | Coefficient of Friction | Mean Deviation of MIU |
| 0.50 osy Wire-Weave w/Meltblown ADH | 0.355 | 0.022 | 0.467 | 0.024 |
| 0.50 osy Wire-Weave w/Strand Coat ADH | 0.397 | 0.015 | 0.374 | 0.012 |
| 0.55 osy Wire-Weave (Erucamide) w/Meltblown ADH | 0.390 | 0.023 | 0.362 | 0.019 |
| 0.55 osy Wire-Wave (Erucamide) w/Strand Coat ADH | 0.362 | 0.018 | 0.347 | 0.015 |
| 0.55 osy Wire-Weave w/Meltblown ADH | 0.463 | 0.025 | 0.366 | 0.020 |
| 0.55 osy Wire-Weave w/Strand Coat ADH | 0.492 | 0.017 | 0.389 | 0.016 |
| 0.55 osy Rib Knit w/Meltblown ADH | 0.376 | 0.026 | 0.389 | 0.021 |
| 0.55 osy Rib Knit w/Strand Coat ADH | 0.377 | 0.019 | 0.393 | 0.017 |
| 0.55 osy EHP w/Meltblown ADH | 0.370 | 0.024 | 0.324 | 0.016 |
| 0.55 osy EHP w/Strand Coat ADH | 0.373 | 0.019 | 0.344 | 0.014 |

As can be seen from Table 1, five different materials were joined using two bonding techniques—strand coating and meltblown control coating. In each instance, the sample made with strand coating had a lower mean deviation of coefficient of friction than the corresponding sample made with the meltblown control coating. Moreover each of the strand coated samples had a mean deviation of less than about 0.020 in the unstretched condition and a mean deviation of less than about 0.018 in the stretched condition.

Shear testing is also used to analyze the shear stiffness of materials. In this test, the specimen is held under a constant tensile force and applied a shear deformation at a constant rate of 0.417 millimeters/second.

The mechanical properties under shear stress are important characteristics of the hand-feel of materials. Shearing stiffiess is the ease with which the fibers slide against each other resulting in soft/pliable to stiff/rigid structures. Lower values of shear stiffness indicate less resistance to shearing movement which corresponds to a softer material having better drape, while higher shear stiffniess indicates lower conformability and bulk softness. The shear stiffniess is used to assess the conformation of the materials to curved surfaces and as an indicator of bulk softness of the materials.

The shear hysteresis (2 HG) is the mean hysteresis at positive and negative shear angles. The larger the value, the worse the recovery ability or less apt the material is to return to its initial state. Shear stiffniess (G), also called "shear rigidity," is calculated as the mean of the slopes of plots of shear force versus shear angle curve. The slopes are obtained at positive shear angle reference (i.e., 0.5 degrees to 2.5 degrees) and negative shear angle reference (i.e., −0.5 degrees to −2.5 degrees). The larger the value, the higher the shearing rigidity or more resistant to deformation the material is. In the shear test, the sample is given a constant tension of 10 gf/cm and then applied a shear deformation at a shear strain rate of 0.417 mm/s A Kawabata Evaluation System (KES-FB-1) shear test model available from Kato Tech Company, Japan, including a Tensile & Shear Electronic Unit, KES Tensile & Shear Mechanical Unit and KES tool kit are used for the testing. The following test procedure is followed:

1. Position the SHEAR/TENSILE function knob on the mechanical unit to the SHEAR position.
2. Toggle the POWER switch to the ON position on the electronic unit and allow the equipment to warm up for a minimum of 15 minutes.
3. The SENS switches are set to the 2 and X5 setting.
4. Turn the OSC/BAL/MES knob to OSC. The needle of the analog meter should be positioned at approximately 10 volts. If it is necessary to adjust the OSC, place a small screwdriver in the OSC adjustment and turn.
5. Turn the OSC/BAL/MES knob to BAL. The needle on the analog meter should be positioned between 0.00 and 0.05 volts. If it is necessary to adjust the BAL, unlock the AC Bal dial, make the necessary adjustment, and relock the dial.
6. Press the black button labeled X.
7. Turn the OSC/BAL/MES knob to MES. The needle on the analog meter should be positioned to approximately 0 volts and the digital readout should read ±0.00. If it is necessary to adjust the MES, unlock the ZERO ADJ dial, make the necessary adjustment, and relock the dial. Leave the OSC/BAL/MES knob positioned to MES.
8. Set the degree of shear deformation by toggling the VAR/SET switch to the appropriate setting and if necessary adjusting the SHEAR CONTROL, SPAN knob to the appropriate degree of shear angle. When a shear deformation of 2 to 7 degrees is desired, toggle the switch to VAR. To adjust the degree of deformation to a setting other than 2 degrees but less than 8 degrees, rotate the SHEAR CONTROL, SPAN knob accordingly.
9. Open the KES program on the computer by double-clicking on the KES-MES VER 7.06E icon.
10. Select Testers(S) from the menu bar at the top of the KES-FB System Measurement Program screen.
11. Select FB1 from the drop-down menu.
12. Select Measurement(M) from the menu bar at the top of the screen.
13. Select Optional Condition, Shear from the drop-down menu.
14. Select the appropriate settings from the following options:
   a. Sample Width: Enter the appropriate specimen width. The width of the specimen refers to the CD direction.
   b. Shear Angle: Enter the degree of shear deformation.
   c. Meas Mode: Select the appropriate mode; 1 cycle is the standard selection.
   d. Repetition: Enter the appropriate number of cycles; 1 is the standard selection. Enter a value no greater than 10 for a cycling test.
15. Loosen the screws on the mechanical unit holding the front and back chucks, if necessary.
16. Toggle the clutch switch to the OFF position.
17. With fingers rotate the front chuck dial so the indicator is aligned with the 0 of the front chuck dial.
18. While holding the front chuck dial in position, toggle the clutch switch to the ON position.
19. Hang the appropriate tension bar by placing the pins into the pin holes located on the front chuck. When testing specimens that are 10 by 10 cm, use the 100 g tension bar. When testing specimens that are 20 by 20 cm, use the 200 g tension bar.
20. Cut the required number of specimens to a minimum dimension of approximately 10 by 10 cm.
21. Enter the appropriate information on the computer for the following:
   a. Direction: Select WARP for the MD testing or WEFT for the CD testing.
   b. Sample No.: In the first input box enter a sample number up to 999. In the second input box enter a specimen number up to 99.
22. On the electronic unit, ensure the digital display reads ±0.00. If not, unlock the ZERO ADJ dial, adjust as necessary, and relock the dial.
23. On the mechanical unit, open the hinged portion of the front chuck and place the specimen through the opening so the edge of the specimen is approximately parallel to the chuck and centered with the center chuck screw. Close the chuck.
24. Carefully open the hinged portion of the back chuck and place the specimen through the opening. Close the chuck. Specimens are usually tested in both the md and cd directions. Either side of the specimen may face upward; test results are not affected.
25. Finger-tighten the screws on the chucks.
26. Electronic unit: Ensure the digital readout displays between ±0.00 and ±0.02. If the digital readout does not display between ±0.00 and ±0.02, loosen the screws on the mechanical unit's front and back chucks, reposition the specimen, and retighten the screws on the chucks. If the digital readout still does not display between ±0.00 and ±0.02 remove the specimen and reposition until the digital readout displays between ±0.00 and ±0.02.

27. Mechanical unit: Toggle the clutch switch to OFF.

28. Electronic unit: Press the black button labeled RES. Press the black button labeled INT.

29. Computer: Select Measure(M) from the menu bar at the top of the KES-FB System Measurement Program FB1-Optional Shear screen.

30. Select Auto Start from the drop-down menu.

31. Change the shear stiffness (G) values to 0.5 in the first input box and 2.5 in the second input box.

32. Change the shear hysteresis (2HG) values to 0.5 in the input box. If the values need to be changed, place the cursor in the appropriate space and type in the appropriate value. Press the Enter key.

33. Record the shear stiffness (G) values.

34. Record the shear hysteresis (2HG) values.

35. Record the degree of shear deformation and the weight of the tension bar used.

36. Repeat the steps for each remaining specimens.

37. Report the mean (M) shear stiffness values (G) to the nearest 0.01 unit.

38. Report the mean (M) shear hysteresis values (2HG) to the nearest 0.01 unit.

39. Report the degree of shear deformation and the weight of the tension bar used.

As shown in Tables 2 and 3, shear testing was performed on a 0.55 osy spunbond panel. In particular, five specimens of a laminate material joined by control coating (Sample 1—code 186) were compared with five specimens of a laminate material formed by strand coating (Sample 2—code 374). As can be seen from Tables 2 and 3, the strand coated sample had a lower shear stiffness in both the machine and cross directions (0.762 g and 1.090 g respectively) than the meltblown control coated sample (1.090 g and 3.040 g), which corresponds to a softer material.

The parameters for the testing were as follows:

Specimen size=10×10 cm

Weight used=100 g

Shear angle=6 degrees

Shear stiffness values of G=0.5, 2.5

Shear stiffness values of 2HG=0.5

TABLE 2

Shear of Materials (Machine Direction)
Parameters
Laboratory Conditions: TAPPI
Specimen size = 10 × 10 cm
Weight used = 100 g
Shear angle = 6 degrees
Shear stiffness values of G = 0.5, 2.5
Shear stiffness values of 2HG = .5

|  | Machine Direction | |
| --- | --- | --- |
|  | Shear Stiffness (G) Mean | Hysteresis (2HG) Mean |
| Sample 1 | | |
| Specimen 1 MD | 0.9 | 1.7 |
| Specimen 2 MD | 0.85 | 2 |
| Specimen 3 MD | 0.9 | 1.85 |
| Specimen 4 MD | 0.83 | 1.75 |
| Specimen 5 MD | 0.8 | 1.8 |
| Average | 0.8560 | 1.8200 |

TABLE 2-continued

Shear of Materials (Machine Direction)
Parameters
Laboratory Conditions: TAPPI
Specimen size = 10 × 10 cm
Weight used = 100 g
Shear angle = 6 degrees
Shear stiffness values of G = 0.5, 2.5
Shear stiffness values of 2HG = .5

|  | Machine Direction | |
| --- | --- | --- |
|  | Shear Stiffness (G) Mean | Hysteresis (2HG) Mean |
| Sample 2 | | |
| Specimen 1 MD | 0.75 | 1.9 |
| Specimen 2 MD | 0.8 | 1.4 |
| Specimen 3 MD | 0.83 | 1.55 |
| Specimen 4 MD | 0.68 | 1.55 |
| Specimen 5 MD | 0.75 | 1.77 |
| Average | 0.7620 | 1.6200 |

TABLE 3

Shear of Materials (Cross Direction)

|  | Cross Direction | |
| --- | --- | --- |
|  | Shear Stiffness (G) Mean | Hysteresis (2HG) Mean |
| Sample 1 | | |
| Specimen 1 CD | 1.18 | 2.85 |
| Specimen 2 CD | 1.2 | 2.9 |
| Specimen 3 CD | 1.35 | 3.4 |
| Specimen 4 CD | 1.35 | 3.4 |
| Specimen 5 CD | 1.13 | 3 |
| Average | 1.2420 | 3.1100 |
| Sample 2 | | |
| Specimen 1 CD | 1.05 | 2.95 |
| Specimen 2 CD | 1.05 | 3.00 |
| Specimen 3 CD | 1.10 | 3.05 |
| Specimen 4 CD | 1.10 | 3.15 |
| Specimen 5 CD | 1.15 | 3.05 |
| Average | 1.09 | 3.0400 |

In addition to the instrument testing, sensory testing was also performed to evaluate the "sensory softness" of strand coated laminates as compared with control coated laminates. The sensory testing was completed using the following methodology:

Panelists:

A panel of twelve (12) people is initially selected. For example, for the testing completed herein, a panel of twelve women were selected. A specialized training session will occur prior to the actual product testing sessions. During this two hour session, the testing procedures will be explained to the panelists as they evaluate a set of practice samples (similar but not identical to the test products).

Sample Preparation:

The test material sections are 10 inches long by 6 inches wide. For example, the sections can be cut from the waist area of absorbent garments. Two sections are bonded to form side seals, such that the sample is two thicknesses of the material and simulates the waist section of an undergarment.

Figure 7:
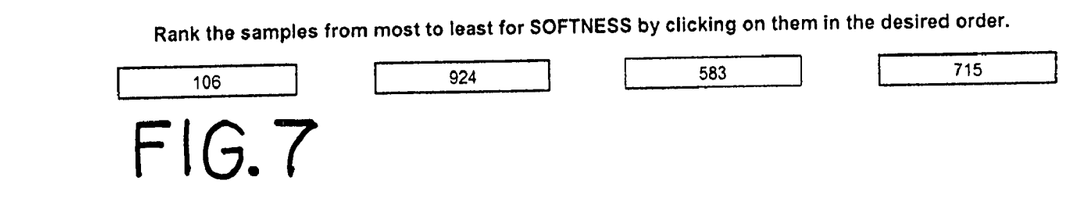
FIG. 7 is a sample ballot for a sensory test.

Scaling Method:

Each panelist evaluates multiple sets of four test products. The panelists order or arrange the products for softness from the most soft to the least soft. The responses are recorded on a computerized ballot, similar to that shown in FIG. 7. Each sample is identified by a 3-digit blinding code. Categorical data is generated that will be analyzed using logistic regression techniques.

Presentation Designs:

An initial presentation set size (block) of four samples is used, since there may be potential difficulties in evaluating multiple samples at one time. When more than four products are to be tested in a study, a balanced incomplete blocks (BIB) can be used.

Panelist Instructions:

A general description of the test procedure is listed below, as it is presented to the panelist.

Overall Softness—The sensory softness of the material, as perceived when gently grasping it with both hands.

Perform the procedure for each individual sample, going left to right. Using both hands, gently grasp the sample from the sides with the thumbs on top and the fingertips below. While moving the fingertips in a circular motion over the surface, evaluate for softness. After feeling each sample once, you may compare any two samples by simultaneously grasping one in the left hand and one product in the right hand. Rank the samples from most to least for Overall Softness Testing Steps:

1. A stack of four samples is presented to each panelist. The panelist receives the stack and arranges the samples left to right, starting from the left (top on left, bottommost on right).
2. The panelist evaluates each product individually starting on the far left and moving in sequence to the right as instructed above.
3. The panelist enters their evaluation on the computerized ballot.

Results:

Sensory testing using the above-referenced methodology evaluated eight test products. The testing was conducted over two days. All eight products were compared by the panelists during each of four sessions (two sessions per day). This allowed for reliability assessments to be made both within testing days and between testing days. For each session, the panelists evaluated six sets of products to rank, each set consisting of a subset of four products. This is a balanced incomplete blocks (BIB) presentation design. Table 4 summarizes the overall design of the study.

Statistical Analysis:

Bases Analysis:

A proportional hazards logistic regression model was used to analyze the ordinal data. All ranking responses were used to generate individual scores for each product that fall along a linear scale. The statistical comparisons between products may be based on data from one or more individual testing sessions, depending on the results of the reliability analyses.

Reliability:

Within-day reliability estimates are made by correlating the two sets of scores made on each day: Session 1 with 2 and Session 3 with 4. The between-day reliability estimates are then made by first collapsing the data within each day and then correlating Day 1 with Day 2. Additional reliability analyses can also be made as the data merit.

Designed Experiment:

Because the eight products were made according to a specified design matrix, a 4 (material)×2 (adhesive style) factorial analysis was conducted that also uses the proportional hazards statistical model. The main effects and the interaction will be assessed to examine the relationships among the product varibles.

The test products are set forth in Table 5.

TABLE 5

Test Products

| Cell | Code | Description |
|---|---|---|
| 1 | 186 | 0.55 osy EHP with Meltblown Adhesive |
| 1 | 374 | 0.55 osy Wire-Weave with Strand Coated Adhesive |
| 1 | 721 | 0.55 osy EHP with Meltblown Adhesive |
| 1 | 812 | 0.55 osy EHP with Strand Coated Adhesive |
| 1 | 239 | 0.55 osy Rib-Knit with Meltblown Adhesive |
| 1 | 493 | 0.55 osy Rib-Knit with Strand Coated Adhesive |
| 1 | 375 | 0.55 osy Wire-Weave (Erucamide) with Meltblown Adhesive |
| 1 | 514 | 0.55 osy Wire-Weave (Erucamide) with Strand Coated Adhesive |

The results of the testing are shown in Tables 6-9.

TABLE 4

Study Design

| | | | | |
|---|---|---|---|---|
| Day 1 | Session 1 | Compare 8 products* | Within-Day Reliability | |
| | Session 2 | Compare 8 products* | | Between-Day Reliability |
| Day 2 | Session 3 | Compare 8 products* | Within-Day Reliability | |
| | Session 4 | Compare 8 products* | | |

*Four products are ranked at one time. Each panelists sees six separate sets of products. Twelve panelists.

TABLE 6

Pairwise Comparisons for Rank Score for Most Soft
Pairwise Comparisons[3]
Rank Score for Most Soft
All Products
Low Score Modeled As Best

| Code | Overall Probability | Log Odds | Standard Error | 95% Grouping | 493 | 812 | 514 | 186 | 375 | 721 | 239 |
|---|---|---|---|---|---|---|---|---|---|---|---|
| 374 | 58.1 | 1.2007 | 0.2358 | A | 74/26.000 | 77/23.000 | 94/6.000 | 100/0.000 | 100/0.000 | 100/0.000 | 100/0.000 |
| 493 | 20.1 | 0.1373 | 0.1785 | B |  | 53/47.442 | 84/16.000 | 99/1.000 | 100/0.000 | 100/0.000 | 100/0.000 |
| 812 | 17.5 | 0.0000 | 0.3011 | B |  |  | 82/18.000 | 99/1.000 | 100/0.000 | 100/0.000 | 100/0.000 |
| 514 | 4.0 | −1.4871 | 0.2211 | C |  |  |  | 96/4.000 | 98/2.000 | 99/1.000 | 99/1.000 |
| 186 | 0.2 | −4.5880 | 0.3842 | D |  |  |  |  | 72/28.000 | 77/23.000 | 83/17.000 |
| 375 | 0.1 | −5.5274 | 0.3954 | C |  |  |  |  |  | 57/43.161 | 65/35.001 |
| 721 | 0.1 | −5.7988 | 0.3982 | E |  |  |  |  |  |  | 58/42045 |
| 239 | 0.0 | −6.1401 | 0.3989 | F |  |  |  |  |  |  |  |

TABLE 7

Summary of the Ordinal Regression Analysis

| Attribute | Product | Sample Size | Prob.† | Linear Score†† | Signif. Grouping |
|---|---|---|---|---|---|
| Softness Day 1 | 0.55 OSY WIRE-WEAV W STRAND COAT ADHES | 96 | 0.59 | 2.5 | a |
|  | 0.55 OSY RIB-KNIT WITH STRAND COAT ADHES | 96 | 0.19 | 1.4 | b |
|  | 0.55 OSY EHP WITH STRAND COATED ADHESIVE | 96 | 0.17 | 1.2 | b |
|  | 0.55 OSY WIR-WEV ERUCAMID W STRA COAT AD | 96 | 0.05 | 0.0 | c |
|  | 0.55 OSY WIRE-WEAVE W MELTBLOWN ADHESIVE | 96 | 0.00 | −2.8 | d |
|  | 0.55 OSY WIR-WEV ERUCAMIDE W MELTBLO ADH | 96 | 0.00 | −3.7 | e |
|  | 0.55 OSY EHP WITH MELTBLOWN ADHESIVE | 96 | 0.00 | −4.1 | ef |
|  | 0.55 OSY RIB-KNIT WITH MELTBLOWN ADHES | 96 | 0.00 | −4.4 | f |
| Softness Day 2 | 0.55 OSY WIRE-WEAV W STRAND COAT ADHES | 96 | 0.61 | 3.2 | a |
|  | 0.55 OSY RIB-KNIT WITH STRAND COAT ADHES | 96 | 0.20 | 2.0 | b |
|  | 0.55 OSY EHP WITH STRAND COATED ADHESIVE | 96 | 0.17 | 1.9 | b |
|  | 0.55 OSY WIR-WEV ERUCAMID W STRA COAT AD | 96 | 0.03 | 0.0 | c |
|  | 0.55 OSY WIRE-WEAVE W MELTBLOWN ADHESIVE | 96 | 0.00 | −3.5 | d |
|  | 0.55 OSY WIR-WEV ERUCAMIDE W MELTBLO ADH | 96 | 0.00 | −4.5 | e |
|  | 0.55 OSY EHP WITH MELTBLOWN ADHESIVE | 96 | 0.00 | −4.7 | ef |
|  | 0.55 OSY RIB-KNIT WITH MELTBLOWN ADHES | 96 | 0.00 | −5.0 | f |

TABLE 8

Summary of the Ordinal Regression Analysis

| Attribute | Product Name | Sam. Size | * | 1 | 2 | 3 | 4 | 5 | 6 | 7 | 8 |
|---|---|---|---|---|---|---|---|---|---|---|---|
| Softness Day 1 | 0.55 OSY WIRE-WEAV W STRAND COAT ADHES | 96 | 1 |  | 76/24 | 78/22 | 92/8 | 100/0 | 100/0 | 100/0 | 100/0 |
|  | 0.55 OSY RIB-KNIT WITH STRAND COAT ADHES | 96 | 2 | 24/76 | — | 53/47 | 80/20 | 99/1 | 99/1 | 100/0 | 100/0 |
|  | 0.55 OSY EHP WITH STRAND COATED ADHESIVE | 96 | 3 | 22/78 | 47/53 | — | 78/22 | 98/2 | 99/1 | 100/0 | 100/0 |
|  | 0.55 OSY WIR-WEV ERUCAMID W STRA COAT AD | 96 | 4 | 8/92 | 20/80 | 22/78 | — | 94/6 | 98/2 | 98/2 | 99/1 |
|  | 0.55 OSY WIRE-WEAVE W MELTBLOWN ADHESIVE | 96 | 5 | 0/100 | 1/99 | 2/98 | 6/94 | — | 71/29 | 77/23 | 83/17 |
|  | 0.55 OSY WIR-WEV ERUCAMIDE W MELTBLO ADH | 96 | 6 | 0/100 | 1/99 | 1/99 | 2/98 | 29/71 | — | 59/41 | 68/32 |

TABLE 8-continued

Summary of the Ordinal Regression Analysis

| Attribute | Product Name | Sam. Size | * | Product Number 1 | 2 | 3 | 4 | 5 | 6 | 7 | 8 |
|---|---|---|---|---|---|---|---|---|---|---|---|
| | 0.55 OSY EHP WITH MELTBLOWN ADHESIVE | 96 | 7 | 0/100 | 0/100 | 0/100 | 2/98 | 23/77 | 41/59 | — | 59/41 |
| | 0.55 OSY RIB-KNIT WITH MELTBLOWN ADHES | 96 | 8 | 0/100 | 0/100 | 0/100 | 1/99 | 17/83 | 32/68 | 41/59 | — |
| Softness Day 2 | 0.55 OSY WIRE-WEAV W STRAND COAT ADHES | 96 | 1 | — | 76/24 | 78/22 | 96/4 | 100/0 | 100/0 | 100/0 | 100/0 |
| | 0.55 OSY RIB-KNIT WITH STRAND COAT ADHES | 96 | 2 | 24/76 | — | 53/47 | 88/12 | 100/0 | 100/0 | 100/0 | 100/0 |
| | 0.55 OSY EHP WITH STRAND COATED ADHESIVE | 96 | 3 | 22/78 | 47/53 | — | 87/13 | 100/0 | 100/0 | 100/0 | 100/0 |
| | 0.55 OSY WIR-WEV ERUCAMID W STRA COAT AD | 96 | 4 | 4/96 | 12/88 | 13/87 | — | 97/3 | 99/1 | 99/1 | 99/1 |
| | 0.55 OSY WIRE-WEAVE W MELTBLOWN ADHESIVE | 96 | 5 | 0/100 | 0/100 | 0/100 | 3/97 | — | 75/25 | 78/22 | 83/17 |
| | 0.55 OSY WIR-WEV ERUCAMIDE W MELTBLO ADH | 96 | 6 | 0/100 | 0/100 | 0/100 | 1/99 | 25/75 | — | 54/46 | 62/38 |
| | 0.55 OSY EHP WITH MELTBLOWN ADHESIVE | 96 | 7 | 0/100 | 0/100 | 0/100 | 1/99 | 22/78 | 46/54 | — | 58/42 |
| | 0.55 OSY RIB-KNIT WITH MELTBLOWN ADHES | 96 | 8 | 0/100 | 0/100 | 0/100 | 1/99 | 17/83 | 38/62 | 42/58 | — |

TABLE 9

Summary of the Ordinal Regression Analysis
HAP-E Study A84113_01 - CHOMP Softer Outer Cover Evaluation

| Attrib. | Product Name | Sample Size | * | Product Number 1 | 2 | 3 | 4 | 5 | 6 | 7 | 8 |
|---|---|---|---|---|---|---|---|---|---|---|---|
| Day 1 | 0.55 OSY WIRE-WEAV W STRAND COAT ADHES | 96 | 1 | — | 0.000 | 0.001 | <.0001 | <.0001 | <.0001 | <.0001 | <.0001 |
| | 0.55 OSY RIB-KNIT WITH STRAND COAT ADHES | 96 | 2 | 0.000 | — | 0.631 | <.0001 | <.0001 | <.0001 | <.0001 | <.0001 |
| | 0.55 OSY EHP WITH STRAND COATED ADHESIVE | 96 | 3 | 0.001 | 0.631 | — | <.0001 | <.0001 | <.0001 | <.0001 | <.0001 |
| | 0.55 OSY WIR-WEV ERUCAMID W STRA COAT AD | 96 | 4 | <.0001 | <.0001 | <.0001 | — | <.0001 | <.0001 | <.0001 | <.0001 |
| | 0.55 OSY WIRE-WEAVE W MELTBLOWN ADHESIVE | 96 | 5 | <.0001 | <.0001 | <.0001 | <.0001 | — | <.0001 | <.0001 | <.0001 |

TABLE 9-continued

Summary of the Ordinal Regression Analysis
HAP-E Study A84113_01 - CHOMP Softer Outer Cover Evaluation

| Attrib. | Product Name | Sample Size | * | Product Number 1 | 2 | 3 | 4 | 5 | 6 | 7 | 8 |
|---|---|---|---|---|---|---|---|---|---|---|---|
| | 0.55 OSY WIR-WEV ERUCAMIDE W MELTBLO ADH | 96 | 6 | <.0001 | <.0001 | <.0001 | <.0001 | <.001 | — | 0.205 | 0.010 |
| | 0.55 OSY EHP WITH MELTBLOWN ADHESIVE | 96 | 7 | <.0001 | <.0001 | <.0001 | <.0001 | <.0001 | 0.205 | — | 0.131 |
| | 0.55 OSY RIB-KNIT WITH MELTBLOWN ADHES | 96 | 8 | <.0001 | <.0001 | <.0001 | <.0001 | <.0001 | 0.010 | 0.131 | — |
| Day 2 | 0.55 OSY WIRE-WEAV W STRAND COAT ADHES | 96 | 1 | — | <.0001 | 0.000 | <.0001 | <.0001 | <.0001 | <.0001 | <.0001 |
| | 0.55 OSY RIB-KNIT WITH STRAND COAT ADHES | 96 | 2 | <.0001 | — | 0.646 | <.0001 | <.0001 | <.0001 | <.0001 | <.0001 |
| | 0.55 OSY EHP WITH STRAND COATED ADHESIVE | 96 | 3 | 0.000 | 0.646 | — | <.0001 | <.0001 | <.0001 | <.0001 | <.0001 |
| | 0.55 OSY WIR-WEV ERUCAMID W STRA COAT AD | 96 | 4 | <.0001 | <.0001 | <.0001 | — | <.0001 | <.0001 | <.0001 | <.0001 |
| | 0.55 OSY WIRE-WEAVE W MELTBLOWN ADHESIVE | 96 | 5 | <.0001 | <.0001 | <.0001 | <.0001 | — | 0.000 | <.0001 | <.0001 |
| | 0.55 OSY WIR-WEV ERUCAMIDE W MELTBLO ADH | 96 | 6 | <.0001 | <.0001 | <.0001 | <.0001 | 0.000 | — | 0.550 | 0.047 |
| | 0.55 OSY EHP WITH MELTBLOWN ADHESIVE | 96 | 7 | <.0001 | <.0001 | <.0001 | <.0001 | <.0001 | 0.550 | — | 0.168 |
| | 0.55 OSY RIB-KNIT WITH MELTBLOWN ADHES | 96 | 8 | <.0001 | <.0001 | <.0001 | <.0001 | <.0001 | 0.047 | 0.168 | — |

Figure 8:
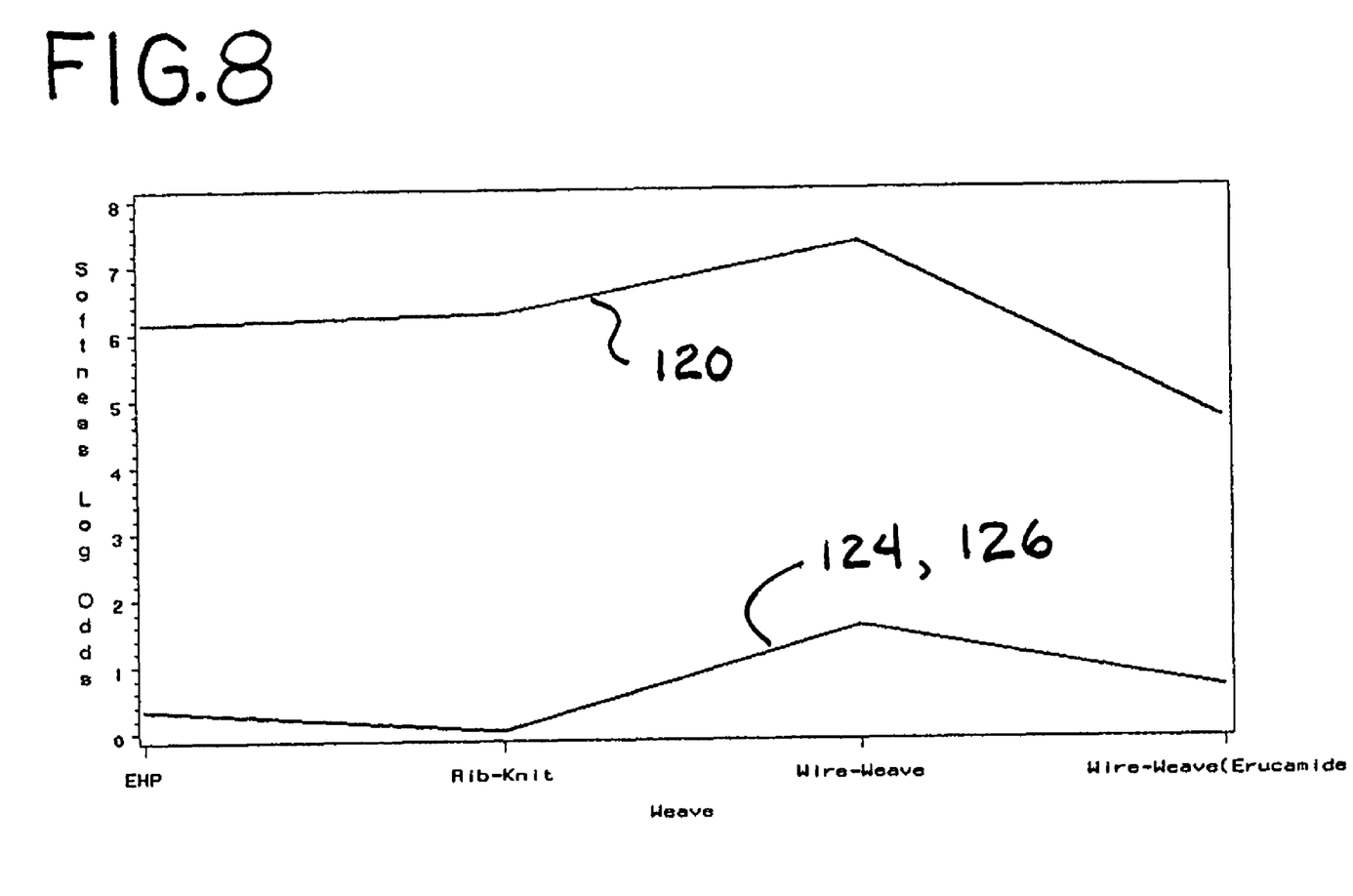
FIG. 8 is a graph of the design effects, including material and adhesive application relative to softness.

As can be seen in Table 6, the comparisons on the right hand side reflect the percent that a particular sample was determined to have a greater sensory softness relative to a comparative sample. For example, the 0.55 osy Wire-Weave material (code 374) with strand coating adhesive was determined to have a greater sensory softness than the 0.55 osy rib-knit material (code 493) joined with strand coated adhesive 75% of the time, and had a greater sensory softness than the corresponding 0.55 osy wire-weave material (code 186) with meltblown control coated adhesive 100% of the time. Indeed, the strand coated wire-weave material (code 374) was determined to have the greatest sensory softness with a 95% confidence (Group A). Referring to the 95% grouping column of Table 6 and also FIG. 8, it is readily apparent that all of the strand coated materials were determined to have a greater sensory softness than all of the control coated materials, and more specifically were determined to have a greater sensory softness than the corresponding materials joined with control coating. As shown in Tables 7-9, the ranking of the materials was consistent from the day 1 and day 2 testing. In addition, the sensory testing correlates with the friction and shear instrument testing.

Other sensory test methods for use in evaluating the softness or other soothing attributes of an article are disclosed in U.S. Patent Publication No. US2004/0003670A1, filed Jan. 8, 2004, which is hereby incorporated herein by reference.

Referring to FIG. 2, the opposite side edges 24 of the front body panel 4 are joined to the opposite side edges 28 of the rear body panel 6 to form a seam. In other embodiments (not shown), fastening members or tabs are attached and extend laterally inboard from the outboard side edge of the front body panel. The fastening members can be configured to releasably engage a portion of the front body panel or the rear body panel. In other embodiments, the fastening members are secured to the rear body panel and releasably engage the front body panel or another portion of the rear body panel. A line of weakness can be provided in one or both of the front and rear body panels to allow the garment to be adjusted using the fastening members after the garment is separated along the line of weakness. In this way, prior to the breaking of the line of weakness, the absorbent garment can be configured as a pant-like garment, which can be pulled over the legs of the user.

In an alternative embodiment, the front and rear body panels are formed integrally, for example as one panel extending around the waist and hips of the user, and then secured, for example by a single side seam.

Referring again to FIGS. 2-5, the absorbent garment includes an absorbent composite 50 having first and second longitudinally opposed terminal end edges 60, 62. The absorbent composite includes a substantially liquid permeable topsheet 134, or liner, and a substantially liquid impermeable backsheet 136, or outer cover. A retention portion 70 is disposed or sandwiched between the topsheet and the backsheet, which are connected. An upper tissue layer 136 is disposed between the retention portion 70 and the single layer 72.

Alternatively, a lower tissue substrate can be disposed adjacent an opposite side of the retention portion, or the tissue can completely envelope the retention position. The topsheet, backsheet and other components of the absorbent composite 50 can be joined for example with adhesive bonds 140, 142, 144, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

Additional layers, including for example, a surge layer 72, can also be incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet.

The backsheet 136 is preferably liquid impermeable, but may be liquid permeable, e.g., when an additional barrier layer is used with the retention portion.

The retention portion 70 is preferably made of an absorbent material, which tends to swell or expand as it absorbs liquid excreted or exuded by the user. For example, the absorbent material can be made of airformed, airlaid and/or wetlaid composites of fibers and high absorbency materials, referred to as superabsorbents. In addition, various foams, absorbent films, and superabsorbent fabrics can be used as an absorbent material.

The retention portion 70 has laterally opposed side edges and preferably is made of a single layer of material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material.

Figure 3:
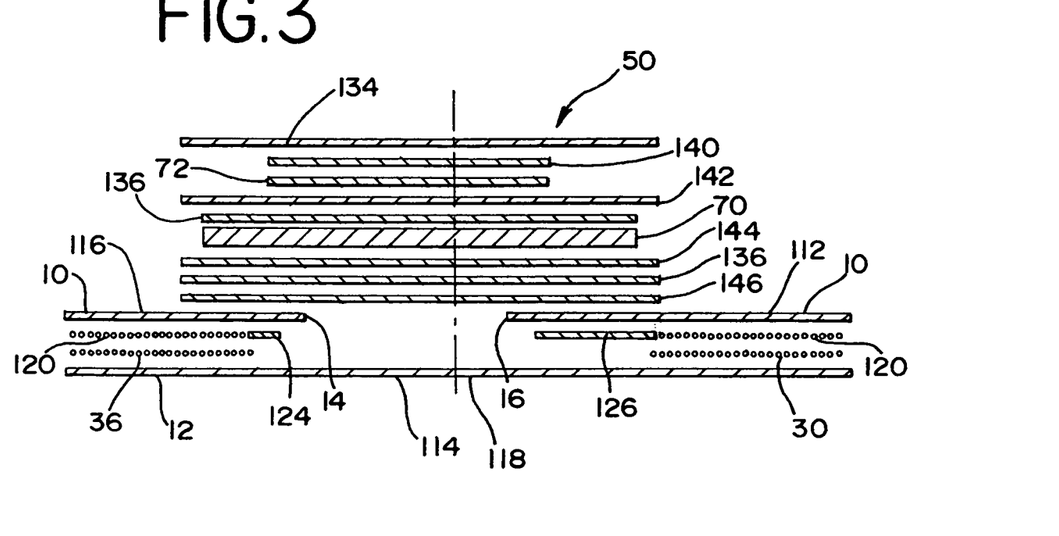
FIG. 3 is a cross-section of the absorbent garment taken along line 3-3 of FIG. 2.
Figure 4:
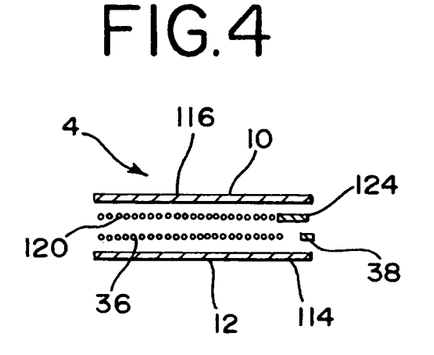
FIG. 4 is a cross-section of the absorbent garment taken along line 4-4 of FIG. 2.
Figure 5:
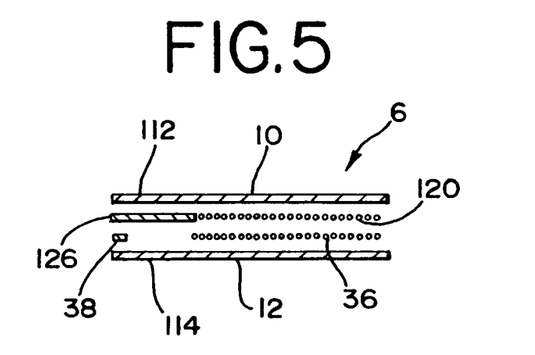
FIG. 5 is a cross-section of the absorbent garment taken along line 5-5 of FIG. 2.

Referring to FIG. 3, the garment side of the absorbent composite, and in particular, the outer, garment side surface of the backsheet 136, is secured to the bodyside surface of the first and second body panels 4, 6 and to the bodyside surface of the crotch portion 118 of the outer cover 114 with an adhesive layer 146. It should be understood that the absorbent composite can be secured using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween.

One suitable absorbent garment construction having front and rear body panels with elastic elements is the Depend® Protective underwear available from Kimberly-Clark Corporation, located in Neenah, Wis. and the Assignee of the present application. In addition, various absorbent garment constructions are disclosed for example and without limitation in U.S. Patent Application Publication US 2003/0135191A1 (Ser. No. 09/899,808), filed Jul. 5, 2001, and U.S. Patent Application Publication US 2003/0088223 (Ser. No. 09/834,682), filed Apr. 13, 2001, the entire disclosures of which are hereby incorporated herein by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An absorbent garment comprising:
a body panel having a terminal waist edge and comprising first and second layers each terminating at said terminal waist edge and at least one waist elastic element disposed between said first and second layers and extending in a lateral direction parallel to said terminal waist edge, wherein said body panel has at least first and second adhesive regions, wherein said first adhesive region is defined by said at least one waist elastic element individually strand coated with a first adhesive, and said second adhesive region is defined by a control coating of a second adhesive applied between said first and second layers.

2. The absorbent garment of claim 1 wherein said first and second adhesives are the same.

3. The absorbent garment of claim 1 wherein said body panel comprises a plurality of spaced apart elastic elements each strand coated with said first adhesive, said plurality of spaced apart elastic elements defining a length of said first adhesive region, wherein said length of said first adhesive region extends to said terminal waist edge of said body panel.

4. The absorbent garment of claim 3 wherein said first adhesive of said strand coated plurality of elastic elements is the only adhesive joining said first and second layers in said first adhesive region.

5. The absorbent garment of claim 3 wherein at least a first portion of said second adhesive region is free of any elastic elements and at least a second portion of said second adhesive region comprises at least one elastic element.

6. The absorbent garment of claim 5 wherein said length of said first adhesive region comprises a first length, and wherein said second adhesive region has a second length that is less than said first length.

7. The absorbent garment of claim 5 wherein said at least one elastic element in said second adhesive region is spaced from and does not intersect any of said plurality of said spaced apart elastic elements in said first adhesive region.

8. The absorbent garment of claim 4 wherein said body panel is stretchable in a lateral direction between an unstretched condition and a stretched condition, wherein said first and second layers comprise spunbond material, and wherein said body panel in said unstretched condition has a surface softness with a mean deviation of coefficient of friction less than about 0.020 in said adhesive region.

9. The absorbent garment of claim 8 wherein said mean deviation of coefficient of friction of said body panel in said stretched condition is less than about 0.018 in said first adhesive region.

10. The absorbent garment of claim 8 wherein an adhesive coverage within said first adhesive region is between about 0.10% and about 6.00% of a total area of said first adhesive region.

11. The absorbent garment of claim 8 wherein said plurality of elastic elements are spaced between about 5 mm and about 15 mm.

12. The absorbent garment of claim 8 wherein said first adhesive region has a greater sensory softness than said second adhesive region.

13. The absorbent garment of claim 1 wherein said first adhesive region has a greater sensory softness than said second adhesive region.

14. The absorbent garment of claim 1 wherein said at least one waist elastic element strand coated with said first adhesive is bonded to both of said first and second layers.

* * * * *